(12) United States Patent
Moriya

(10) Patent No.: US 8,705,820 B2
(45) Date of Patent: Apr. 22, 2014

(54) LESION AREA EXTRACTION APPARATUS, METHOD, AND PROGRAM

(75) Inventor: Yoshiyuki Moriya, Minato-ku (JP)

(73) Assignee: FUJIFILM Corporation, Tokyo (JP)

(*) Notice: Subject to any disclaimer, the term of this patent is extended or adjusted under 35 U.S.C. 154(b) by 589 days.

(21) Appl. No.: 12/895,028

(22) Filed: Sep. 30, 2010

(65) Prior Publication Data

US 2011/0075913 A1      Mar. 31, 2011

(30) Foreign Application Priority Data

Sep. 30, 2009  (JP) ................................ 2009-226102
Mar. 30, 2010  (JP) ................................ 2010-077346

(51) Int. Cl.
*G06K 9/00*      (2006.01)

(52) U.S. Cl.
USPC ......................................................... 382/128

(58) Field of Classification Search
None
See application file for complete search history.

(56) References Cited

U.S. PATENT DOCUMENTS

| | | | | |
|---|---|---|---|---|
| 7,599,534 B2* | 10/2009 | Krishnan | ...................... | 382/128 |
| 7,876,939 B2* | 1/2011 | Yankelevitz et al. | ......... | 382/128 |
| 2005/0207630 A1* | 9/2005 | Chan et al. | .................... | 382/131 |
| 2007/0237377 A1* | 10/2007 | Oosawa | ........................ | 382/128 |
| 2008/0044080 A1* | 2/2008 | Li | ............................... | 382/155 |
| 2009/0185731 A1* | 7/2009 | Ray et al. | ..................... | 382/131 |
| 2010/0158332 A1* | 6/2010 | Rico et al. | ..................... | 382/128 |
| 2010/0250275 A1 | 9/2010 | Sakagawa et al. | | |
| 2010/0256991 A1 | 10/2010 | Ishikawa et al. | | |
| 2011/0075913 A1* | 3/2011 | Moriya | ......................... | 382/132 |
| 2012/0035963 A1* | 2/2012 | Qian et al. | ........................ | 705/3 |

FOREIGN PATENT DOCUMENTS

| | | |
|---|---|---|
| JP | 2007-68554 A | 3/2007 |
| JP | 2009086750 A | 4/2009 |
| JP | 2009095550 A | 5/2009 |
| WO | WO 2010/109351 A1 * | 2/2010 |

OTHER PUBLICATIONS

Hara et al., "Automated Lesion Detection Methods for 2D and 3D Chest X-Ray Images," International Conference on Image Analysis and Processing, 768-773, (1999).*
Notice of Grounds for Rejection dated Sep. 17, 2013, issued in Japanese Patent Application No. 2010-077346.

* cited by examiner

*Primary Examiner* — Tahmina Ansari
(74) *Attorney, Agent, or Firm* — Sughrue Mion, PLLC

(57) ABSTRACT

Recording a plurality of lesion area extraction processing data generated in advance according to a plurality of types of lesion areas, recording a radiology which includes a character string having a lesion description character and being related to position information of a lesion area in the medical image, determining lesion area extraction processing data used for the extraction from the plurality of lesion area extraction processing data based on the lesion description character provided in the radiology report, and performing the extraction using the determined lesion area extraction processing data and the position information of the lesion area related to the character string.

18 Claims, 5 Drawing Sheets

LESION AREA EXTRACTION APPARATUS, METHOD, AND PROGRAM

BACKGROUND OF THE INVENTION

1. Field of the Invention

The present invention relates to a lesion area extraction apparatus and method using a radiology report of a medical image. The invention also relates to a computer readable recording medium on which is recorded a program for causing a computer to perform the method.

2. Description of the Related Art

In medical image diagnosis, it is often the case that image reading is performed by a radiologist and the result of the reading is recorded and reported to the attending doctor as a radiology report, in which electronic radiology reports are widely used.

As one of such radiology reports, a report in which a lesion description character is linked to a reference image that includes the lesion area is known. Use of such radiology report allows the attending doctor to click on the lesion description character in the report displayed on a screen to display and observe a corresponding reference image, thereby facilitating the understanding of the radiology report by the attending doctor.

In the image diagnosis, it is also practiced to evaluate the malignancy of a lesion or to decide the treatment policy based on the size or progress of the lesion in the medical image. For such medical diagnosis, it is necessary to accurately extract a lesion area from a medical image. One lesion area extraction method is known as described, for example, in U.S. Patent Application Publication No. 20080044080 in which an arbitrary point is specified by the user in a lesion area of a medical image, a discrimination area is set with reference to the specified point, an evaluation is made as to whether or not each pixel in the discrimination area is a pixel representing the contour of the lesion area, and the contour of the lesion area is determined based on the evaluation result. Here, the evaluation as to whether or not each pixel in the discrimination area is a pixel representing the contour of the lesion area is made by an evaluation function obtained through machine learning of multiple sample images, each including a lesion area with a known contour.

In the mean time, extraction of a contour of a lesion area is conducted, in U.S. Patent Application Publication No. 20080044080, using the same evaluation function regardless of the type of lesion.

Lesion areas, however, differ in characteristics from type to type and the method that extracts all types of lesion areas by the same evaluation function described above does not fully make use of the characteristics of the respective lesion areas, leading to the degradation in extraction performance of a lesion area.

In view of the circumstances described above, it is an object of the present invention to provide a lesion area extraction apparatus and method capable of improving the extraction performance of a lesion area. It is a further object of the present invention to provide a computer readable recording medium on which is recorded a program for causing a computer to perform the method.

SUMMARY OF THE INVENTION

A lesion area extraction apparatus of the present invention is an apparatus for extracting a lesion area from a medical image, the apparatus, including:

an extraction process recording means for recording a plurality of lesion area extraction processing data generated in advance according to a plurality of types of lesion areas;

a report recording means for recording a radiology report which includes a character string having a lesion description character and being related to position information of a lesion area in the medical image;

an extraction process determination means for determining lesion area extraction processing data used for the extraction from the plurality of lesion area extraction processing data recorded on the extraction process recording means based on the lesion description character provided in the radiology report; and an area extraction means for performing the extraction using the determined lesion area extraction processing data and the position information of the lesion area related to the character string.

The term "lesion area extraction processing data" as used herein refers to a wide range of information data required for extracting a lesion area from a medical image. Lesion area extraction processing data generated for a specific type of lesion area is lesion area extraction processing data generated by giving particular consideration to the characteristics of the specific type of lesion areas and is capable of extracting a lesion area of the specific type. An evaluation function obtained by machine learning a plurality of sample images in advance, each including, for example, a lesion area of a type called chest nodule to evaluate whether or not each pixel of a medical image is a pixel representing a contour of the chest nodule is one such example.

The apparatus described above may further include a display means for displaying the radiology report and a specification means for specifying the character string in the displayed radiology report, the extraction process determination means may be a means that determines lesion area extraction processing data based on the lesion description character of the specified character string, and the area extraction means may be a means that extracts the lesion area using the determined lesion area extraction processing data and the position information of the lesion area related to the specified character string.

Further, the report recording means may be a means that further records a second radiology report generated, at a different time, for the same patient as the one of a first radiology report which is the radiology report, the character string may be a character string also related to a second character string, having a lesion description character, provided in the second radiology report, and, when the character string is related to the second character string, the extraction process determination means may be a means that determines the lesion area extraction processing data based on the lesion description character of the second character string.

Still further, the report recording means may be a means that further records a second radiology report generated, at a different time, for the same patient as the one of a first radiology report which is the radiology report, and the apparatus may be an apparatus further includes an obtaining means for, when a character describing a lesion at a position corresponding to the position of a lesion area is provided in the second radiology report, obtaining lesion area extraction processing data for the described lesion, a judgment means for judging whether or not the lesion area extraction processing data obtained by the obtaining means corresponds to the lesion area extraction processing data determined by extraction process determination means, and a warning means for issuing a warning if the judgment made by the judgment means is not corresponding.

A lesion area extraction method of the present invention is a method for extracting a lesion area from a medical image, the method including the steps of:

recording, on a extraction process recording means, a plurality of lesion area extraction processing data generated in advance according to a plurality of types of lesion areas; recording, on a report recording means, a radiology report which includes a character string having a lesion description character and being related to position information of a lesion area in the medical image;

determining lesion area extraction processing data used for extracting the lesion area from the plurality of lesion area extraction processing data recorded on the extraction process recording means based on the lesion description character provided in the radiology report; and extracting the lesion area using the determined lesion area extraction processing data and the position information of the lesion area related to the character string.

The method describe above may further include the steps of displaying the radiology report and specifying the character string in the displayed radiology report, the step of determining lesion area extraction processing data may be a step in which the determination is performed based on the lesion description character of the specified character string, and the step of extracting the lesion area may be a step in which the lesion area is extracted using the determined lesion area extraction processing data and the position information of the lesion area related to the specified character string.

Further, the method may further include the step of recording a second radiology report generated, at a different time, for the same patient as the one of a first radiology report which is the radiology report, and, when the character string is a character string related to a second character string, having a lesion description character, provided in the second radiology report, the step of determining lesion area extraction processing data may be a step in which the lesion area extraction processing data is determined based on the lesion description character of the second character string.

Still further, the method may further includes the steps of recording a second radiology report generated, at a different time, for the same patient as the one of a first radiology report which is the radiology report, when a character describing a lesion at a position corresponding to the position of a lesion area is provided in the second radiology report, obtaining lesion area extraction processing data for the described lesion, judging whether or not the obtained lesion area extraction processing data corresponds to the determined lesion area extraction processing data, and issuing a warning if the judgment made in the judgment step is not corresponding.

A computer readable recording medium of the present invention is a medium on which is recorded a lesion area extraction program of the present invention for causing a computer to function as the extraction process recording means, report recording means, extraction process determination means, and area extraction means of the lesion area extraction apparatus described above.

The program described above may be a program that further causes the computer to function as the display means for displaying the radiology report and the specification means for specifying the character string in the displayed radiology report of the lesion area extraction apparatus described above.

Further, the program described above may be a program that still further causes the computer to function as the obtaining means, judgment means, and warning means of the lesion area extraction apparatus described above.

The program is supplied to the user recorded on a recording medium, such as CD-ROM or DVD or recorded in downloadable to a built-in disk of a server computer or a network storage device.

In the apparatus, method, and program described above, the term "type of lesion area" refers to the type of lesion indicated by the lesion area, and the type includes, by way of example, brain tumor, chest nodule, liver tumor, liver cyst, and kidney cyst.

The term "position information of a lesion area" as used herein refers to information indicating an arbitrary point in the lesion area or the area.

The term "character string specification" as used herein refers to that a character string is specified by a mouse, a keyboard, or another input device.

The term "lesion description character" as used herein refers to a character describing the lesion which includes, for example, any of the lesion name, a key word or a symbol representing the lesion name, and an abbreviation thereof.

The term "corresponding position" as used herein refers to the identical position or an adjacent position thereof.

According to the lesion area extraction apparatus, method, and program of the present invention, when extracting a lesion area from a medical image, lesion area extraction processing data used for extracting the lesion area from a plurality of lesion area extraction processing data generated in advance based on a lesion description character provided in a radiology report with respect to the lesion area, and the lesion area is extracted suing the determined lesion area extraction processing data. This allows each lesion area to be extracted by making full use of characteristics of each lesion area, whereby area extraction accuracy may be improved.

Further, the lesion area is extracted using the position information of the lesion area related to a character string of a radiology report, so that the user does not need to directly specify an arbitrary point in the lesion area, whereby the work load of the user may be reduced.

Further, in the lesion area extraction apparatus, method, and program described above, if a radiology report is displayed, then a character string is specified in the displayed radiology report, lesion area extraction processing data is determined based on the lesion description character of the specified character string, and the lesion area is extracted using the determined lesion area extraction processing data and the position information of the lesion area related to the specified character string, the lesion area corresponding to the lesion description character of the character string may be extracted accurately by making full use of the characteristics of the lesion area. Further, by displaying the extracted lesion area, radiology report generation or observation efficiency may be improved.

Still further, where the character string is related to a second character string having a lesion description character provided in a second radiology report generated, at a different time, for the same patient as the one of a first radiology report which is the radiology report thereof, if lesion area extraction processing data is determined based on the lesion description character of the second character string, the lesion area may be extracted by the same lesion area extraction processing data as that used for extracting the related lesion area observed at a different time. In particular, where character strings describing the same lesion are related to each other, the lesion area may be extracted by the same lesion area extraction processing data as that used for extracting an area of the same lesion observed at a different time.

Further, where a character describing a lesion at a position corresponding to the position of the lesion area is provided in a second radiology report generated, at a different time, for the same patient as the one of a first radiology report which is the radiology report thereof, if an arrangement is adopted in which lesion area extraction processing data for the described lesion is obtained, then a judgment is made whether or not the obtained lesion area extraction processing data corresponds to the determined lesion area extraction processing data, and a warning is issued the judgment made is not corresponding, then when the determined lesion area extraction processing data differs from the lesion area extraction processing data for a lesion which is highly likely the same lesion observed at a different time, revision of the determined lesion area extraction processing data may be prompted by issuing a warning. This allows modification to be made in the determined lesion area extraction processing data according to the user input in response to the warning.

DESCRIPTION OF THE PREFERRED EMBODIMENTS

Figure 1:
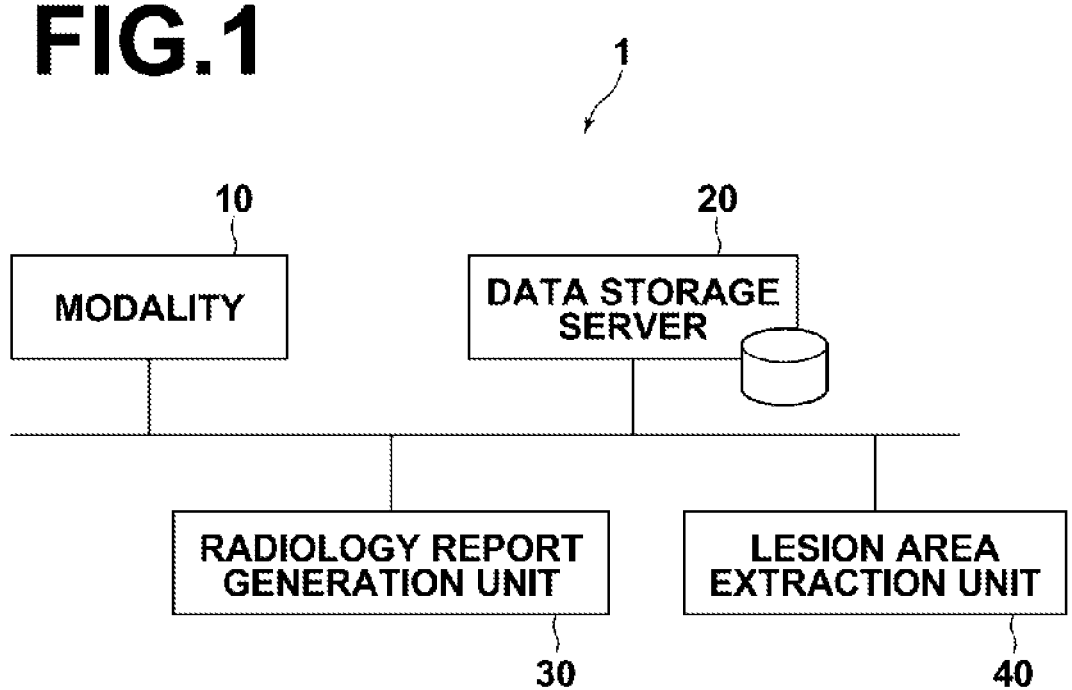
FIG. 1 is a schematic configuration diagram of an embodiment of the lesion area extraction apparatus of the present invention.

Hereinafter, embodiments of the present invention will be described with reference to the accompanying drawings. FIG. 1 is a block diagram of a medical image processing system, schematically illustrating the configuration thereof. As shown in FIG. 1, the system includes modality 10, data storage server 20, radiology report generation unit 30, and lesion area extraction unit 40 which are communicatably linked to each other via network 9.

Modality 10 is a system for generating a medical image representing a test body, and more specifically it is a CT system, MRI system, PET, ultrasonic diagnostic system, or the like. The image generated by modality 10 is sent to data storage server 20 and stored therein.

Data storage server 20 is a computer for storing/managing various types of data and communicates with other components via network 9 to send/receive image data and the like. More specifically, a medical image generated by modality 10, a radiology report generated by radiology report generation unit 30, and the like are obtained through network 9, stored in a recording medium, such as a hard disk, and managed. Further, server 20 retrieves data in response to a retrieval request from the other system component, such as radiology report generation unit 30 or lesion area extraction unit 40, and sends the extracted data to the system component that has made the retrieval request.

Since data storage server 20 includes medial images and radiology reports with tag information identifying respective patients attached thereto, a medical image and a radiology report of the same patient can be easily retrieved and extracted for use using the tag information.

The image data storage format and communication between each component of the system via network 9 is based on DICOM protocol or the like.

Figure 2:
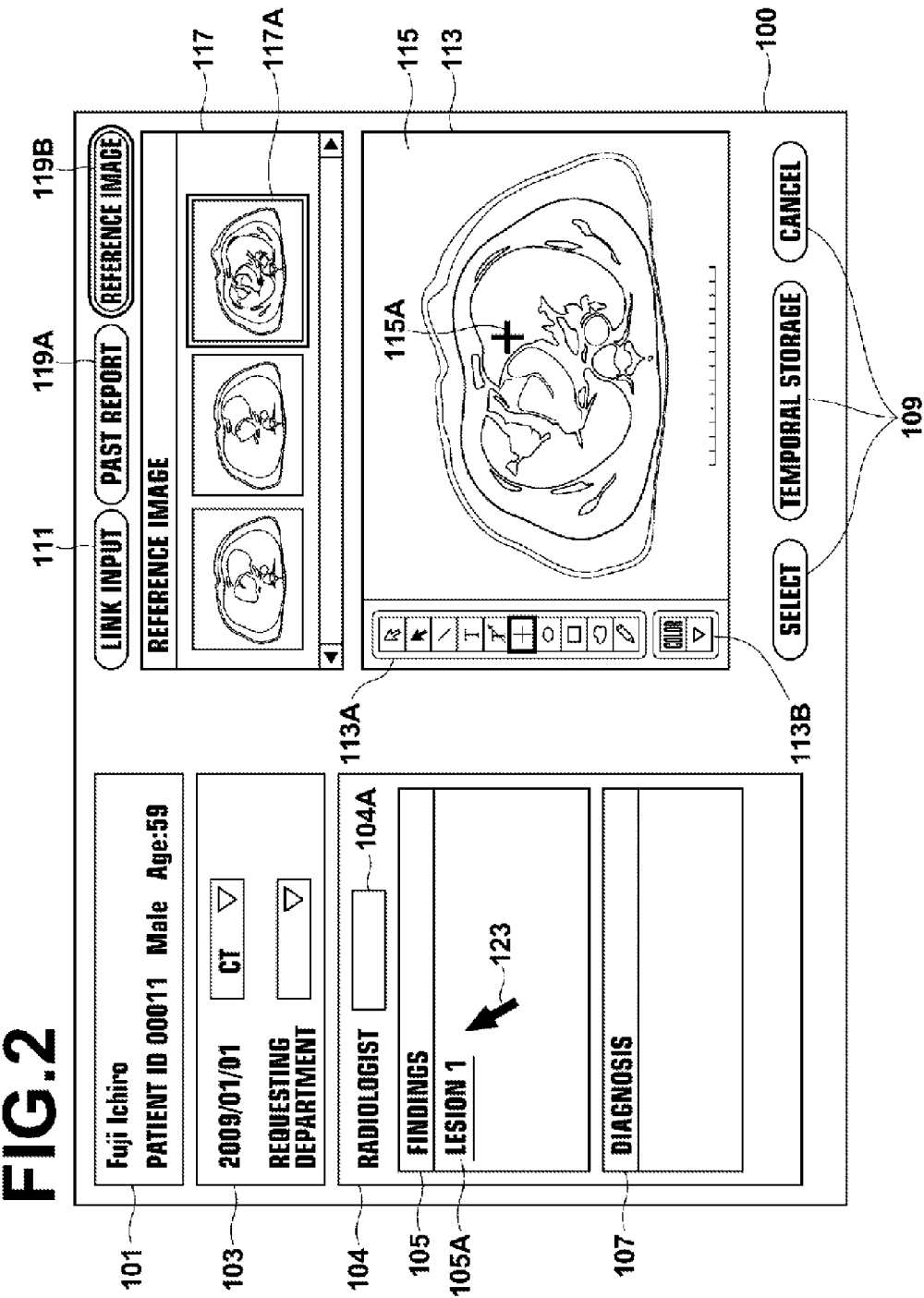
FIG. 2 shows an example screen for generating a radiology report.
Figure 4:
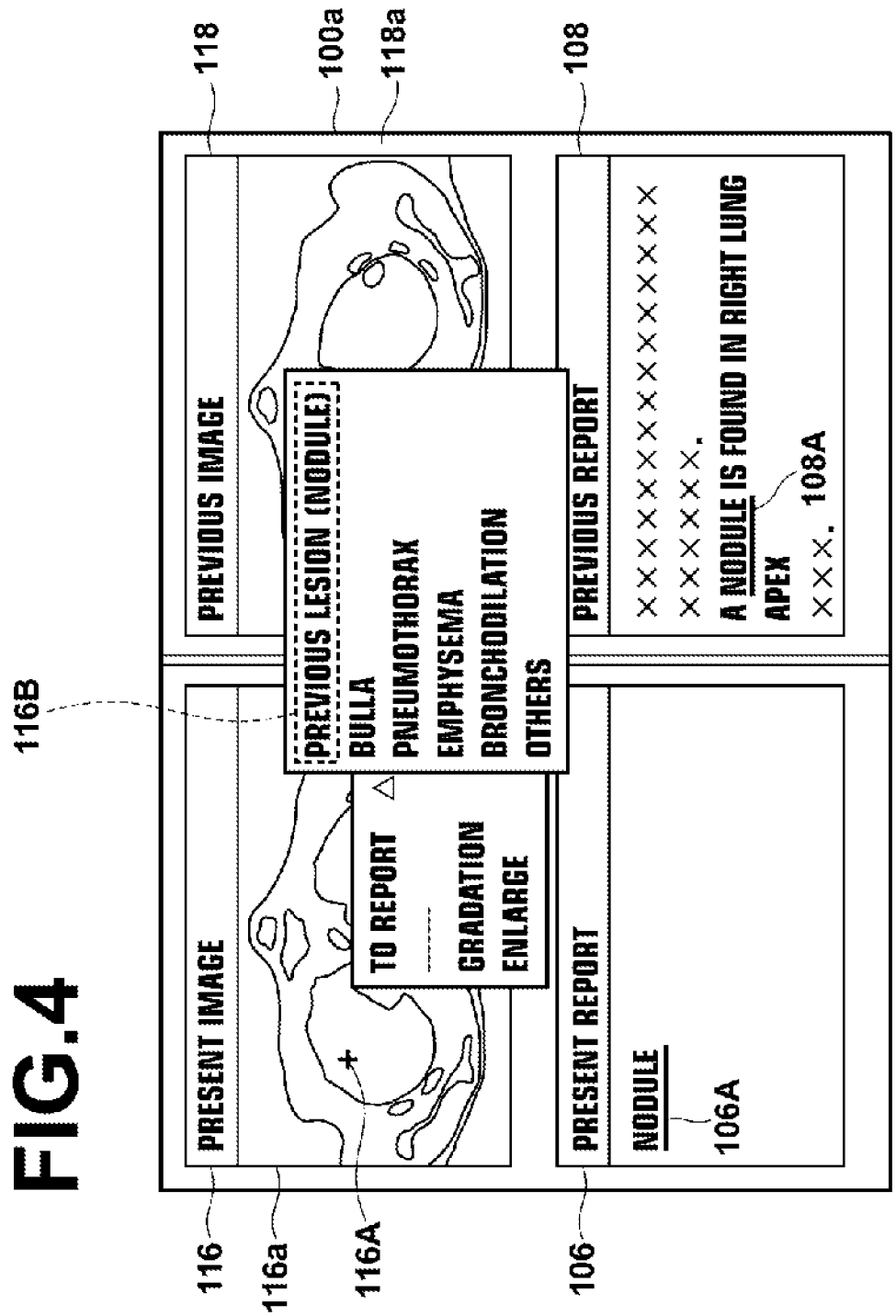
FIG. 4 shows an example screen for generating a radiology report.

Radiology report generation unit 30 displays, for example, radiology report generation screen 100 or 100a shown in FIG. 2 or 4, and generates an electronic radiology report of a medical image according to user input operation in the generation screen. For that purpose, unit 30 includes: a display, such as a liquid crystal display or the like, for performing various type of displays; an input device of a keyboard, a mouse, and the like for use by the user to input various instructions; a hard disk for storing various types of data including image data and radiology reports; a memory in which a radiology report generation program is stored; a CPU for controlling the radiology report generation unit by executing the program stored in the memory; and a communication interface linked to network 9 via a bus.

Radiology report generation unit 30 may generate a radiology report in which a character string is related by hyperlink to a medical image, position information of a lesion area of the medical image, or a character string of another radiology report. The attending doctor or the like may click on the character string (link character) of the radiology report on the screen to display a medical image or the like related to the character string on the display.

In the present application, a link character not related to a character string of another radiology report is called a first class link character and that related to a character string of another radiology report is called a second class link character.

First, radiology report generation screen 100 and processing for providing a first class link character in a radiology report according to user input operation will be described.

Radiology report generation screen 100 includes patient information area 101 for providing patient information, medical image information area 103 for providing medical image information, radiology report area 104, and the like. With respect to radiologist name field 104A, finding field 105 which is a radiology report, and diagnostic field 107 provided in radiology report area 104, information may be inputted and edited by a doctor or the like as the operator using a mouse, a keyboard, or the like. In addition, radiology report generation screen 100 includes link input selection button 111 that allows a link character linked by hyperlink to a medical image to be inputted in finding field 105.

Radiology report generation screen 100 further includes radiology report editing button 109 for storing or canceling an edited radiology report, past report selection button 119A for referencing various types of information, and reference image selection button 119B. For example, if reference image selection button 119B is operated, thumbnails of medical images are selectably displayed in reference information area 117, as shown in FIG. 2, and when one of the thumbnails is further selected, medical image 115 corresponding to selected thumbnail 117A is displayed in detailed image display area 113. Detailed image display area 113 is provided with editing buttons 113A and 113B for processing and editing the medical image.

Next, processing performed in radiology report generation unit 30 for providing a link character 105A corresponding to a first class link character in finding field 105 will be described. First, link input button 111 is selected to set the link input mode to ON. Then, when a cross pointer is placed on the position of a lesion and mouse clicked, the link character 105A linked to medical image 115, including the position 115A of the lesion, is related to position information that indicates the position of the lesion area, such as the coordinates thereof, in the medical image 115 and inserted in finding field 105. Here, the link character 105A is inserted in finding field 105 in a manner so as to be distinguishable from other characters and a second class link character, such as coloring, underlining, or the like, in order to indicate that the link character 105A is linked.

Figure 3:
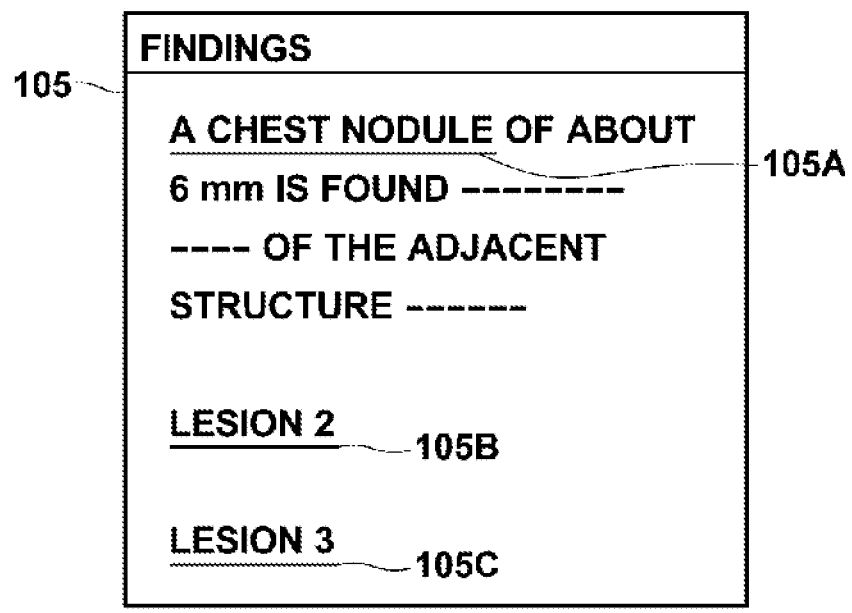
FIG. 3 shows an example screen for generating a radiology report.

In radiology report generation unit 30, a fixed character string, such as lesion 1 or lesion 2, is inserted as the link character 105A only by specifying the position of a lesion area, so that the operator may edit the inserted link character and a text around the character or may insert a different link character through the use of a keyboard or the like later. FIG. 3 shows an example of finding field 105 of radiology report generation screen 100. The example finding field of FIG. 3 includes three different link characters lesion 1 (105A), lesion 2 (105B), and lesion 3 (105C) and shows that lesion 1 (105A) is changed to "chest nodule (105A)" which are the characters of more specifically describing the lesion 1.

When a doctor generating or observing the radiology report specifies a first class link character, a medical image linked to the link character is displayed on the display and an indicator, such as a cross mark, an arrow, or the like, indicating the position of the lesion is displayed on the medical image.

Next, radiology report generation screen 100a and processing for providing a second class link character in a radiology report according to user input operation will be described.

Radiology report generation screen 100a includes, on the left side, present image area 116 for displaying present image 116a which is a medical image obtained through the present inspection and the target of radiology reading and present report area 106 for displaying a present report which is a radiology report generated by performing radiology reading of the present image. While, the screen 100a includes, on the right side, past image area 118 for displaying past image 118a which is a medical image obtained through the previous inspection with respect to the same patient and previous report area 108 for displaying a previous report which is a radiology report generated by performing radiology reading on the previous image. With respect to present image area 116 and present report area 106, information may be inputted and edited by a doctor or the like as the operator using a mouse, a keyboard, or the like.

Next, processing performed in radiology report generation unit 30 for providing a link character 106A corresponding to a second class link character in finding field 106 will be described. When a cross pointer is placed on the position of a lesion in a present image 116a and the right button of a mouse is clicked, a list of selection items, such as "To Report", "Gradation", "Enlargement", and the like is displayed in pull-down menu format, and if a selection item of "To Report" is selected, a list of character string candidates to be inserted in finding field 106 is displayed in pull-down menu format.

As the candidates to be inserted, the list displays as selection items, for example, lesion names, such as bulla, pneumothorax, emphysema, bronchodilation, and the like in addition to a link character and the like provided in the previous report. FIG. 4 shows an example case in which a link character of nodule (108A) is provided in the previous report and a selection item of "previous lesion (nodule)" representing the link character is included in the list. Here, the description will be made on the assumption that the link character "nodule" (108A) is a first class link character related to position information of a lesion area in the previous image.

The user moves the selection frame 116B upward or downward by keyboard or mouse operation to select a character string to be inputted to finding field 106 and the selection is finalized. For example, if a keyboard is used, the selection is finalized by pressing the "Enter" key. It is noted that when selection frame 116B is on a selection item of "previous lesion (nodule)", the link character "nodule" (108A) in the previous report corresponding to the selection item is highlighted.

As for the selection item representing the link character provided in the previous report, all link characters provided in the previous report may be employed or only a link character provided in relation to the position in the previous image corresponding to the position 116A in the right-mouse clicked present image may be employed. The corresponding positions as used herein refer to the same or adjacent positions.

Next, when "previous lesion (nodule)" is selected from the displayed list and the selection is finalized, a link character (106A) of "nodule" is inserted in the present report area 106 which is related to the link character "nodule" (108A) in the previous report corresponding to the selected item. Further, the link character "nodule" (106A) is related to position information, such as the coordinates, of position 116A of lesion area in the present image 116a on which the right button of the mouse is clicked. The link character 106A is inserted in a manner so as to be distinguishable from other characters and a first class link character, such as coloring, underlining, or the like, in order to indicate that the link character is linked to a character string in another radiology report.

When a doctor generating or observing the radiology report specifies a second class link character of "nodule" (106A), a present image 106a linked to the link character is displayed on the display and an indicator, such as a cross mark, an arrow, or the like, indicating the position 116A of the lesion is displayed in the present image 106a. Further, the previous image 118a linked to the character string "nodule" (108A) in the previous report which is in turn linked to the link character "nodule" (106A) is displayed on the display and an indicator, such as a cross mark, an arrow, or the like indicating the position of the lesion is displayed in the previous image 118a. As a result, comparative observation of a temporal change in the nodule, which is a common lesion between the present and previous images, can be made easily.

Here, the description has been made of a case in which the previous report is made referable when generating a present report by performing radiology reading of the present image, but not limited to this, and a radiology report generated in the past for the same patient as that of the present report to be generated can be made referable for generating the present report.

When a plurality of inspections is performed for the same patient and a radiology report is generated with respect to each medical image obtained in each inspection, radiology report generation unit 30 provides a list of link characters, like that shown in Table 1, used in each radiology report.

TABLE 1

| LINK CHARACTER | INSPECTION DATE AND TIME | | | |
|---|---|---|---|---|
| | 2008 Feb. 13 | 2008 Jan. 22 | 2007 Oct 12 | 2007 Jul. 13 |
| NODULE | ○ | ○ | ○ | ○ |
| PLEURAL EFFUSION | ○ | ○ | | |
| PNEUMONIA | | ○ | | |

In Table 1, "○" mark represents a link character provided in each radiology report. Further, by providing each "○" mark with the same link as that of each corresponding link character, the linked medical image, the position of a lesion, and the like may be displayed on the display when either one of "◯" marks is specified by the user, like when the corresponding link character is specified in a radiology report displayed on the screen.

Further, each data of inspection (2008.02.13, or the like) in Table 1 may be provided with links to corresponding medical image and radiology report to allow the user, when the user specifies any one of the dates of inspection, to display the medical image and radiology report corresponding to the date of inspection specified by the user. Further, a configuration may be adopted in which, when any one of link characters (nodule and the like) is specified, a list of medical images of the lesion corresponding to the link character is displayed to facilitate understanding of a temporal change in the lesion.

Figure 5:
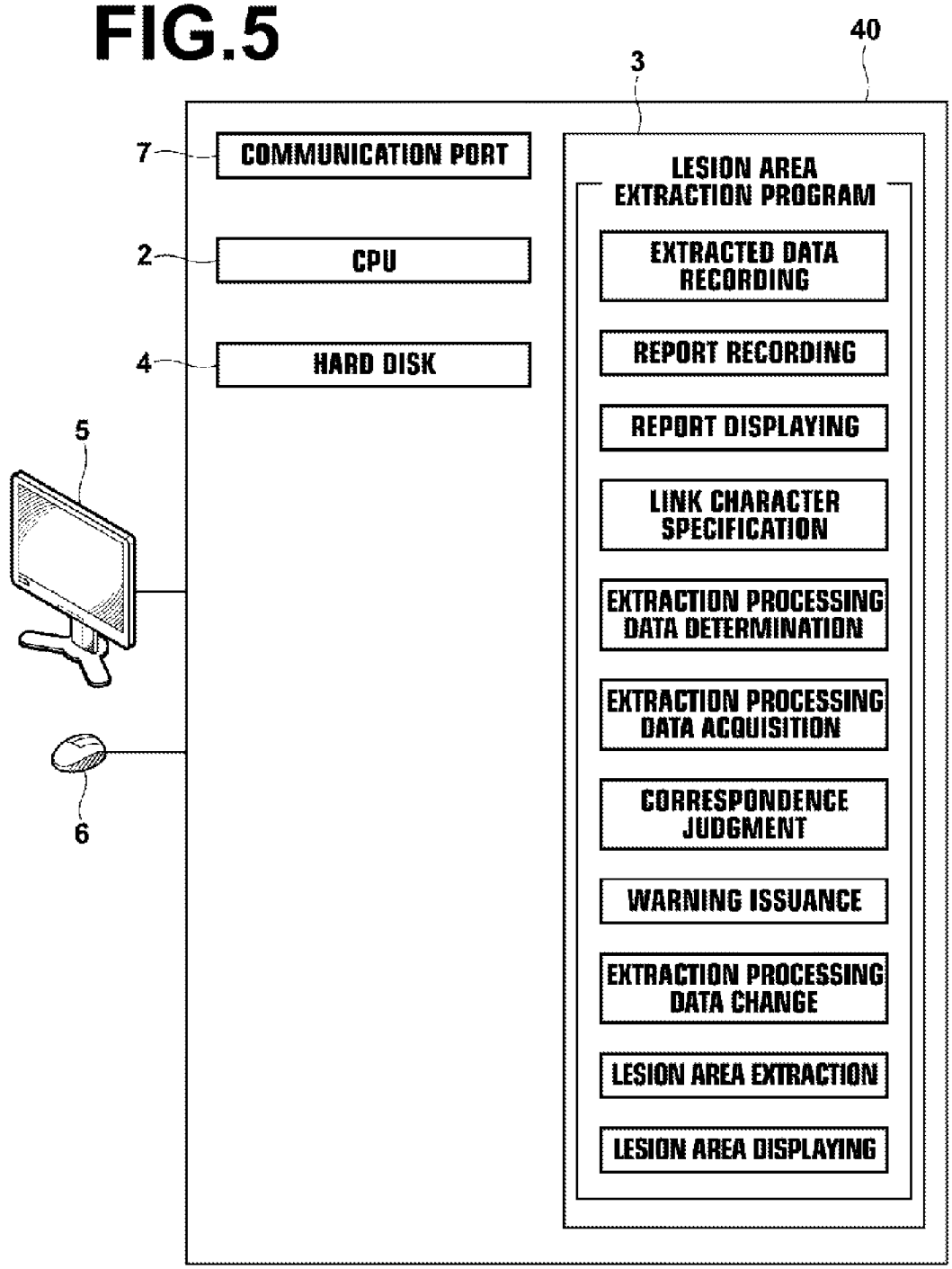
FIG. 5 is a block diagram of the lesion area extraction apparatus.

As a standard computer configuration, lesion area extraction unit 40 includes CPU 2, memory 3, hard disk 4, and communication port 7, as illustrated in FIG. 5. Further, display 5 and an input device, such as mouse 6, are connected to lesion area extraction unit 40.

A lesion area extraction program is stored in memory 3. The lesion area extraction program defines, as processes executed by CPU 2, an extraction processing data recording process, a report recording process, a report display process, a link character specification process, an extraction processing data determination process, an extraction processing data obtaining process, a judgment process, a warning process, an extraction processing data changing process, a lesion area extraction process, a lesion area displaying process, and the like. When these processes are executed by CPU 2 according to the program, a general purpose computer functions as a display means, a specification means, an extraction process recording means, a report recording means, an extraction process determination means, an obtaining means, a judgment means, a warning means, a changing means, area extraction means, and the like.

Hard disk 4 includes a plurality of lesion area extraction processing data, each being generated according to each of a plurality of types of lesion areas, radiology reports obtained from data storage server 20 and the like via network 9, and the like.

Specific processing performed by lesion area extraction unit 40 for extracting a lesion area from a medical image will now be described.

First, prior to initiating the lesion area extraction process, lesion area extraction unit 40 records, on hard disk 4, a plurality of lesion area extraction processing data, each being generated in advance according to each of a plurality of types of lesion areas. Here, each of the plurality of lesion area extraction processing data is an evaluation function obtained with respect to each type of lesions, such as brain tumor, chest nodule, liver tumor, liver cyst, kidney cyst, and the like through machine learning a plurality of sample images which include each type of lesion area in advance to evaluate whether or not each pixel in a medical image is a pixel representing a contour of each type of lesion area. Each of the evaluation functions may be obtained through machine learning based on, for example, the AdaBoosting algorithm described in U.S. Patent Application Publication No. 20080044080.

Then, lesion area extraction unit 40 obtains (records) and displays a radiology report in response to a request from the operator. Lesion area extraction unit 40 obtains a particular radiology report corresponding to the operator's request from data storage server 20 or radiology report generation unit 30 via communication port 7, and records the obtained radiology report on hard disk 4, as well as displaying on the display 5.

The identification of the radiology report is based on input of specifying patient name information, patient ID, inspection ID, or radiology report ID.

Then, in the particular radiology report (target report) displayed on display 5, a specification process for specifying a link character is performed. For example, in response to the selection, by the operator, of any of link characters provided in the finding filed of the target report with the input device such as mouse 6, the clicked link character is specified. Here, it is assumed that one or more of either or both of first and second class link characters are included in the radiology report and the link character specified by the operator is a first class link character or a second class link character.

Next, based on the link character specified by the link character specification process, lesion area extraction unit 40 performs a process for determining lesion area extraction processing data used for extracting the lesion area from a plurality of lesion area extraction processing data recorded on hard disk 4. The process of determining the lesion area extraction processing data when the link character specified in the link character specification process is a first class link character differs from the process when the link character specified in the link character specification process is a second class link character. Therefore, each case will be described hereinafter.

First, the case in which the link character specified by the link character specification process is a first class link character will be described. When a first class link character is specified by the link character specification process, lesion area extraction unit 40 performs a process of determining the lesion area extraction processing data based on a lesion description character in the specified link character. More specifically, with respect to each of a plurality of types of lesions, lesion description character that includes, for example, any of the lesion name, a key word or a symbol representing the lesion name, and an abbreviation thereof is related to one of a plurality of lesion area extraction processing data recorded on hard disk 4 which seems to be most appropriate for extracting a lesion area of the type indicated by the lesion description character and registered in advance, and the lesion area extraction processing data corresponding to the lesion description character of the link character is selected from the registered list of lesion description characters. In order to prevent retrieval omission, it is preferable to also register a synonym (Japanese/English) of each registered lesion description character as being representing each registered lesion description character, thereby performing the retrieval based on each registered lesion description character and the list of the synonyms.

Then, the lesion area extraction processing data retrieved as being related to the lesion description character is determined to be the lesion area extraction processing data for extracting the lesion area. For example, lesion description characters of brain tumor, chest nodule, liver tumor, liver cyst, and kidney cyst are related to lesion area extraction process function F1 obtained in advance through machine learning of a plurality of sample images of brain tumor, lesion area extraction process function F2 obtained in advance through machine learning of a plurality of sample images of chest nodule, lesion area extraction process function F3 obtained in advance through machine learning of a plurality of sample images of liver tumor, and lesion area extraction process function F4 obtained in advance through machine learning of a plurality of sample images of liver cyst, and lesion area extraction process function F5 obtained in advance through machine learning of a plurality of sample images of kidney cyst respectively and registered in advance. Then, in the link character specification process, when, for example, the link character (105A) formed of a character string of "chest nodule" in FIG. 3 is specified, the lesion area extraction process function F2 related to the lesion description character, that is, "chest nodule" is determined to be the lesion area extraction process function for extracting the lesion area.

Where no matching lesion description character is found, a lesion description character having highest similarity to the character string may be retrieved. Alternatively, a list of lesion description character candidates may be displayed in pull-down menu format to have the operator to select a lesion description character having highest association from the list and the lesion area extraction processing data related to the selected lesion description character is determined to be the lesion area extraction processing data for extracting the lesion area. Here, if a lesion description character is selected from the list of lesion description character candidates displayed in pull-down menu format, the selection result is recorded and when the same link character is specified in the subsequent processing, the lesion area extraction processing data to be used is determined based on the recorded selection result.

Next, the case in which the link character specified by the link character specification process is a second class link character will be described. When a second class link character is specified by the link character specification process, each lesion area extraction unit 40 performs a process of determining the lesion area extraction processing data based on a lesion description character in a character string in another radiology report related to the specified link character. For example, when a link character "previous lesion" related to a link character "nodule" in another radiology report of the same patient generated at different time is found in the target report, and the link character "previous lesion" is specified in the link character specification process, a region description character corresponding to the link character "nodule" in another radiology report related to the specified link character "previous lesion" is retrieved from the list of lesion description characters registered on hard disk 4 in advance and lesion area extraction processing data related to the corresponding lesion description character is determined to be the lesion area extraction processing data for extracting the lesion area.

That is, the second case differs from the first case where the first class link character is specified on which link character is used to determine the lesion area extraction processing data. But, the process of determining a most appropriate extraction processing data from a plurality of lesion area extraction processing data registered on hard disk 4 in advance is common, and with respect to the common process, various technical aspects employed in the case where the first class link character is specified may be applied directly.

Further, lesion area extraction unit 40 has a function to select a more detailed lesion area extraction processing data based on the lesion area extraction processing data determined based on each link character (first class link character or second class link character) in the manner as described above or to change a parameter of the lesion area extraction processing data based on information tagged to a medical image (DICOM information, such as slice interval and the like) linked to the link character.

Here, the term "select a more detailed lesion area extraction processing data" as used herein refers to, if, for example, a first chest nodule lesion area extraction processing data (chest nodule 1) obtained by machine learning sample images with a slice interval of 5 mm or greater and a second chest nodule lesion area extraction processing data (chest nodule 2) obtained by machine learning sample images with a slice interval of less than 5 mm are provided as chest nodule lesion area extraction processing data, that either chest nodule 1 (slice interval of 5 mm or greater) or chest nodule 2 (slice interval of less than 5 mm) is selected.

The term "change a parameter" as used herein refers to set spacing or a slice interval, a slice thickness, or the like to the lesion area extraction processing data as a parameter.

When a character describing a lesion located at a position corresponding to the position of the lesion area (position of target lesion) related to the specified link character is found in another radiology report of the same patient as that of the target report, lesion area extraction unit 40 performs a judgment process for judging whether or not the process of obtaining the lesion area extraction processing data for the described lesion, the obtained lesion area extraction processing data, and the determined lesion area extraction processing data are matched, and a warning process for issuing a warning if they do not match in the judgment.

More specifically, a judgment is made as to whether or not a lesion is present at a position corresponding to the position of the target lesion. For example, when a previous image and a previous report, which is a radiology report of the previous image, for the same patient as that of the target report are stored in data storage server 20, all link characters provided in the previous report are obtained and, based on position information of lesion area in the previous image related to each link character, a judgment is made as to which of the positions is identical to the position of the target lesion or an adjacent position thereof. Preferably, the judgment is made after aligning the previous image with the medical image that includes the target lesion using an image alignment technology described, for example, in Japanese Unexamined Patent Publication No. 2007-068554 to match the reference position in position coordinates between each image.

As a result of the judgment, if no lesion is found at a position corresponding to the position of the target lesion or an adjacent position thereof, a judgment is made that no lesion is present at the corresponding position, and subsequent obtaining process for obtaining lesion area extraction processing data, judgment process, and warning process are not performed. On the other hand, if a lesion is found at a position corresponding to the position of the target lesion or an adjacent position thereof, a judgment is made that the lesion present at the position corresponding to the position of the target lesion or an adjacent position thereof is the lesion present at the corresponding position. Where two or more lesions are present at the position corresponding to the position of the target lesion or an adjacent position thereof, a lesion located at a position closest to the position of the target lesion is determined to be the lesion at the corresponding position.

Next, the lesion area extraction processing data for the lesion judged to be present at the corresponding position is obtained. If any of lesion area extraction processing data was applied to the lesion in the past and the history thereof is recorded, the lesion area extraction processing data applied in the past is obtained. If no such history is recorded, the lesion area extraction processing data determination process described above is applied to the link character in the previous report with respect to the lesion to obtain the most appropriate extraction processing data for extracting the area.

Then, a judgment is made as to whether or not the obtained lesion area extraction processing data corresponds to the lesion area extraction processing data determined in the lesion area extraction processing data determination process. If the judgment result shows that they correspond to each other, the subsequent warning process is not performed. On the other hand, if they do not correspond to each other, a warning is issued to notify the user of the disagreement. For example, a message prompting review of the determined lesion area extraction processing data is displayed on display 5. In this case, it is preferable that the lesion area extraction processing data obtained for the lesion at the corresponding position is also displayed.

When an instruction to change the lesion area extraction processing data is inputted by the user in response to the outputted warning, lesion area extraction unit 40 performs a process of changing the extraction processing data according to the instruction. For example, according to the instruction from the user, the determined lesion area extraction processing data may be changed to lesion area extraction processing data obtained for the lesion at the corresponding position or another lesion area extraction processing data stored in hard disk 4. When the lesion area extraction processing data is changed, the changed lesion area extraction processing data is used for an area extraction process to be described later. In the mean time, if a change instruction is not inputted by the user or an instruction to continue the processing without change is inputted, the subsequent processing is continued without changing the lesion area extraction processing data.

The obtaining process, judgment process, warning process, and changing process may be performed only when the link character specified in the link character specification process is a first class link character.

Then, an area extraction process is performed using the lesion area extraction processing data determined in the extraction processing data determination process (if changed after the determination, then the changed lesion area extraction processing data) and position information of the lesion area related to the link character specified in the link character specification process. More specifically, with reference to the position of the lesion area related to the link character, a judgment area, including the lesion area, is set in the medical image. As for the judgment area, for example, an area greater than a maximum possible size of the lesion area is set with the position of the lesion area in the center. Then, a characteristic amount of each pixel in the judgment area is obtained in order to evaluate whether or not each pixel is a pixel representing a contour of the lesion area. The characteristic amount is determined according to the lesion area extraction processing data used for the evaluation, such as luminance information of an adjacent area of each pixel. Next, based on the obtained characteristic amount, an evaluation value that indicates whether or not each pixel in the judgment area is a pixel representing a contour of the lesion area using the lesion area extraction processing data determined in the extraction process determination process. Then, based on the evaluation value calculated for each pixel, the lesion area is extracted by dynamic programming or graph cut method described, for example, in U.S. Patent Application Publication No. 20080044080.

Then, lesion area extraction unit 40 performs a process of displaying a medical image in which the extracted lesion area is presented in a manner distinguishable from other areas with a radiology report thereof on display 5.

According to the lesion area extraction unit, method, and program of the present embodiment, a doctor generating or observing a radiology report may easily refer to the size or progress of a lesion by specifying the link character of the lesion provided in the finding field of the radiology report, so that the doctor may generate or observe the radiology report more efficiently. Further, each lesion area is extracted by fully utilizing the characteristics thereof, whereby region extraction accuracy may be improved.

In the embodiment described above, the description has been made of a case in which, in response to the specification of a link character by the operator, a lesion area corresponding to the specified link character is extracted. But an arrangement may be adopted in which, when a radiology report is obtained from data storage server 20 or the like, a process for extracting a lesion area corresponding to each of all link characters included in the radiology report is performed and the extraction result of lesion areas are recorded on hard disk 4 or the like to allow them to be outputted in various forms desired by the operator at a later time.

What is claimed is:

1. A lesion area extraction apparatus for extracting a lesion area from a medical image, the apparatus comprising:
    an extraction process recording means for recording a plurality of lesion area extraction processing data generated in advance according to a plurality of types of lesion areas;
    a report recording means for recording a radiology report which includes a character string having a lesion description character and being related to position information of a lesion area in the medical image;
    an extraction process determination means for determining, based on the lesion description character provided in the radiology report, one of the plurality of lesion area extraction processing data to be used to extract the lesion area; and
    an area extraction means for performing the extraction using the determined lesion area extraction processing data and the position information of the lesion area related to the character string.

2. The lesion area extraction apparatus of claim 1, wherein:
    the apparatus further comprises a display means for displaying the radiology report and a specification means for specifying the character string in the displayed radiology report;
    the extraction process determination means is a means that performs the determination based on the lesion description character of the specified character string; and
    the area extraction means is a means that performs the extraction using the determined lesion area extraction processing data and the position information of the lesion area related to the specified character string.

3. The lesion area extraction apparatus of claim 1, wherein:
    the report recording means is a means that further records a second radiology report generated, at a different time, for the same patient as the one of a first radiology report which is the radiology report;
    the character string is a character string also related to a second character string, having a lesion description character, provided in the second radiology report; and
    when the character string is related to the second character string, the extraction process determination means is a means that determines the lesion area extraction processing data based on the lesion description character of the second character string.

4. The lesion area extraction apparatus of claim 1, wherein:
    the report recording means is a means that further records a second radiology report generated, at a different time, for the same patient as the one of a first radiology report which is the radiology report; and
    the apparatus further comprises:
    an obtaining means for, when a character describing a lesion at a position corresponding to the position of a lesion area is provided in the second radiology report, obtaining lesion area extraction processing data for the described lesion;

a judgment means for judging whether or not the lesion area extraction processing data obtained by the obtaining means corresponds to the lesion area extraction processing data determined by extraction process determination means; and a warning means for issuing a warning if the judgment made by the judgment means is not corresponding.

5. The lesion area extraction apparatus of claim 2, wherein:
the report recording means is a means that further records a second radiology report generated, at a different time, for the same patient as the one of a first radiology report which is the radiology report;

the character string is a character string also related to a second character string, having a lesion description character, provided in the second radiology report; and when the character string is related to the second character string, the extraction process determination means is a means that determines the lesion area extraction processing data based on the lesion description character of the second character string.

6. The lesion area extraction apparatus of claim 2, wherein:
the report recording means is a means that further records a second radiology report generated, at a different time, for the same patient as the one of a first radiology report which is the radiology report; and the apparatus further comprises:

an obtaining means for, when a character describing a lesion at a position corresponding to the position of a lesion area is provided in the second radiology report, obtaining lesion area extraction processing data for the described lesion;

a judgment means for judging whether or not the lesion area extraction processing data obtained by the obtaining means corresponds to the lesion area extraction processing data determined by extraction process determination means; and a warning means for issuing a warning if the judgment made by the judgment means is not corresponding.

7. A lesion area extraction method for extracting a lesion area from a medical image, the method comprising the steps of:

recording, on a extraction process recording means, a plurality of lesion area extraction processing data generated in advance according to a plurality of types of lesion areas;

recording, on a report recording means, a radiology report which includes a character string having a lesion description character and being related to position information of a lesion area in the medical image;

an extraction process determination means for determining, based the lesion description character provided in the radiology report, one of the plurality of lesion area extraction processing data to be used to extract the lesion area and performing the extraction using the determined lesion area extraction processing data and the position information of the lesion area related to the character string.

8. The lesion area extraction method of claim 7, wherein:
the method further comprising the steps of displaying the radiology report and specifying the character string in the displayed radiology report;

the step of determining lesion area extraction processing data is a step in which the determination is performed based on the lesion description character of the specified character string; and the step of performing the extraction is a step in which the extraction is performed using the determined lesion area extraction processing data and the position information of the lesion area related to the specified character string.

9. The lesion area extraction method of claim 7, wherein:
the method further comprises the step of recording a second radiology report generated, at a different time, for the same patient as the one of a first radiology report which is the radiology report; and when the character string is a character string related to a second character string, having a lesion description character, provided in the second radiology report, the step of determining lesion area extraction processing data is a step in which the lesion area extraction processing data is determined based on the lesion description character of the second character string.

10. The lesion area extraction method of claim 7, further comprising the steps of:

recording a second radiology report generated, at a different time, for the same patient as the one of a first radiology report which is the radiology report;

when a character describing a lesion at a position corresponding to the position of a lesion area is provided in the second radiology report, obtaining lesion area extraction processing data for the described lesion;

judging whether or not the obtained lesion area extraction processing data corresponds to the determined lesion area extraction processing data; and issuing a warning if the judgment made in the judgment step is not corresponding.

11. The lesion area extraction method of claim 8, wherein:
the method further comprises the step of recording a second radiology report generated, at a different time, for the same patient as the one of a first radiology report which is the radiology report;

when the character string is a character string related to a second character string, having a lesion description character, provided in the second radiology report, the step of determining lesion area extraction processing data is a step in which the lesion area extraction processing data is determined based on the lesion description character of the second character string.

12. The lesion area extraction method of claim 8, further comprising the steps of:

recording a second radiology report generated, at a different time, for the same patient as the one of a first radiology report which is the radiology report;

when a character describing a lesion at a position corresponding to the position of a lesion area is provided in the second radiology report, obtaining lesion area extraction processing data for the described lesion;

judging whether or not the obtained lesion area extraction processing data corresponds to the determined lesion area extraction processing data; and issuing a warning if the judgment made in the judgment step is not corresponding.

13. A non-transitory computer readable recording medium on which is recorded a program for causing a computer to function as a lesion area extraction apparatus for extracting a lesion area from a medical image, the program causes the computer to function as:

an extraction process recording means for recording a plurality of lesion area extraction processing data generated in advance according to a plurality of types of lesion areas;

a report recording means for recording a radiology report which includes a character string having a lesion description character and being related to position information of a lesion area in the medical image;

an extraction process determination means for determining, based on the lesion description character provided in the radiology report, one of the plurality of lesion area extraction processing data to be used to extract the lesion area; and an area extraction means for performing the extraction using the determined lesion area extraction processing data and the position information of the lesion area related to the character string.

14. The recording medium of claim 13, wherein:

the program is a program further causes the computer to function as a display means for displaying the radiology report and a specification means for specifying the character string in the displayed radiology report;

the extraction process determination means is a means that performs the determination based on the lesion description character of the specified character string; and the area extraction means is a means that performs the extraction using the determined lesion area extraction processing data and the position information of the lesion area related to the specified character string.

15. The recording medium of claim 13, wherein:

the report recording means is a means that further records a second radiology report generated, at a different time, for the same patient as the one of a first radiology report which is the radiology report;

the character string is a character string also related to a second character string, having a lesion description character, provided in the second radiology report; and when the character string is related to the second character string, the extraction process determination means is a means that determines the lesion area extraction processing data based on the lesion description character of the second character string.

16. The recording medium of claim 13, wherein:

the report recording means is a means that further records a second radiology report generated, at a different time, for the same patient as the one of a first radiology report which is the radiology report; and the program is a program that further causes the computer to function as:

an obtaining means for, when a character describing a lesion at a position corresponding to the position of a lesion area is provided in the second radiology report, obtaining lesion area extraction processing data for the described lesion;

a judgment means for judging whether or not the lesion area extraction processing data obtained by the obtaining means corresponds to the lesion area extraction processing data determined by extraction process determination means; and a warning means for issuing a warning if the judgment made by the judgment means is not corresponding.

17. The recording medium of claim 14, wherein:

the report recording means is a means that further records a second radiology report generated, at a different time, for the same patient as the one of a first radiology report which is the radiology report;

the character string is a character string also related to a second character string, having a lesion description character, provided in the second radiology report; and when the character string is related to the second character string, the extraction process determination means is a means that determines the lesion area extraction processing data based on the lesion description character of the second character string.

18. The recording medium of claim 14, wherein:

the report recording means is a means that further records a second radiology report generated, at a different time, for the same patient as the one of a first radiology report which is the radiology report; and the program is a program that further causes the computer to function as:

an obtaining means for, when a character describing a lesion at a position corresponding to the position of a lesion area is provided in the second radiology report, obtaining lesion area extraction processing data for the described lesion;

a judgment means for judging whether or not the lesion area extraction processing data obtained by the obtaining means corresponds to the lesion area extraction processing data determined by extraction process determination means; and a warning means for issuing a warning if the judgment made by the judgment means is not corresponding.

* * * * *